United States Patent [19]

Ohta et al.

[11] Patent Number: 5,230,026

[45] Date of Patent: Jul. 20, 1993

[54] APPARATUS FOR DISCRIMINATING PARTICLE AGGREGATION PATTERN

[75] Inventors: Masato Ohta; Yasuhiko Yokomori; Toshiyuki Furuta; Hideo Suda; Naoki Ozawa; Shogo Kida, all of Kanagawa, Japan

[73] Assignee: Suzuki Motor Corporation, Shizuoka, Japan

[21] Appl. No.: 700,618

[22] Filed: May 15, 1991

[30] Foreign Application Priority Data

May 18, 1990 [JP] Japan ................................ 2-128646

[51] Int. Cl.[5] ............................................. B60K 9/00
[52] U.S. Cl. ......................................... 382/6; 356/39; 364/555
[58] Field of Search ................................ 382/6, 50, 53; 364/413.08, 413.1, 555, 525, 554; 356/39; 358/107, 903

[56] References Cited

U.S. PATENT DOCUMENTS

| | | | |
|---|---|---|---|
| 4,060,713 | 11/1977 | Golay | 382/6 |
| 4,097,845 | 6/1978 | Racus | 382/6 |
| 4,207,554 | 6/1980 | Resnick et al. | 382/6 |
| 4,319,271 | 3/1982 | Hurni et al. | 358/107 |
| 4,453,266 | 6/1984 | Bacus | 382/6 |
| 4,592,089 | 5/1986 | Hartman | 382/6 |
| 4,794,450 | 12/1988 | Saito et al. | 356/39 |
| 5,040,112 | 8/1991 | Marshall et al. | 364/413.08 |
| 5,096,835 | 5/1992 | Yokomori et al. | 364/555 |

*Primary Examiner*—Jose L. Couso
*Attorney, Agent, or Firm*—Flynn, Thiel, Boutell & Tanis

[57] ABSTRACT

An apparatus for discriminating a particle aggregation pattern includes a memory circuit for storing line data output from a CCD line sensor, which line data represents the aggregation pattern. A maximum value is obtained for each set of line data, and thereafter a further maximum value is obtained from the afore-mentioned previously obtained maximum values. A threshold value is determined on the basis of the further maximum value, and is then applied to the line data in order to extract therefrom information regarding the shape and area of the aggregation pattern. In another embodiment, the threshold value is determined on the basis of minimum values obtained from the line data.

10 Claims, 6 Drawing Sheets

FIG. 10 PRIOR ART (AGGREGATION IMAGE PORTION)
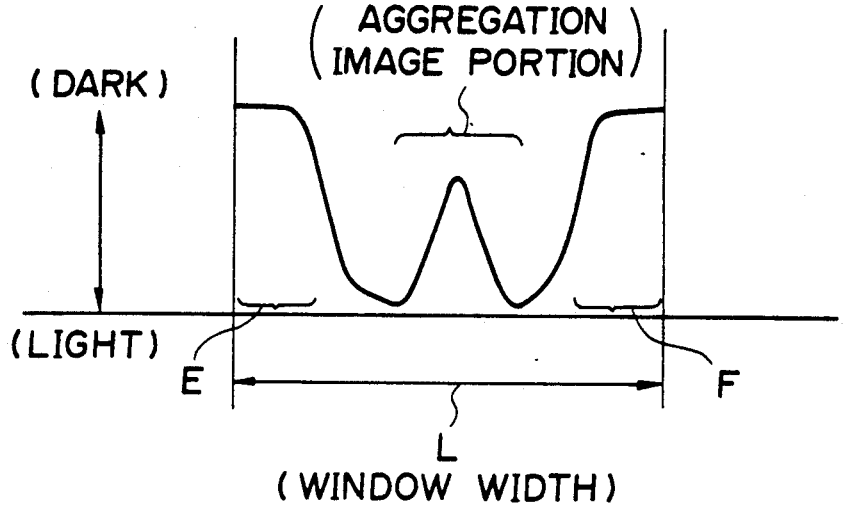
FIG. 11 PRIOR ART
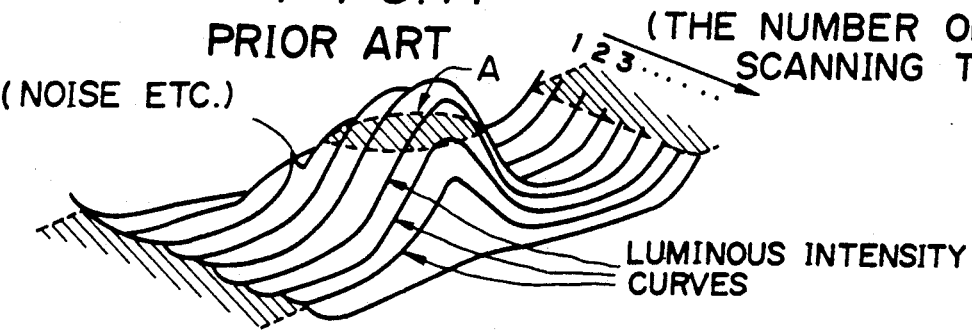
FIG. 12 PRIOR ART (CROSS SECTIONAL VIEW AT THRESHOLD LEVEL)
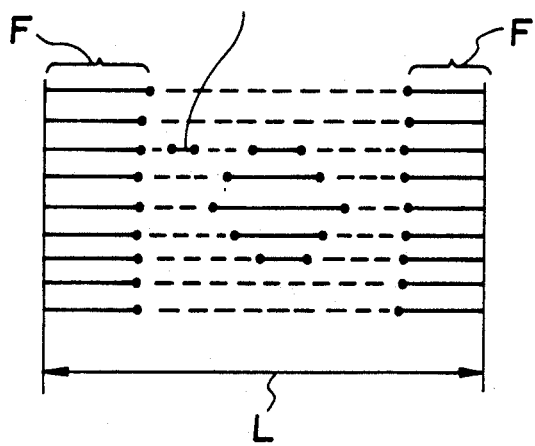
E, F : PORTIONS OTHER THAN PATTERN
SOLID LINE : LINE AREA DATA

APPARATUS FOR DISCRIMINATING PARTICLE AGGREGATION PATTERN

CROSS REFERENCE TO RELATED APPLICATION

This application is related to copending U.S. Ser. No. 07/520,093 filed on May 7, 1990.

FIELD OF THE INVENTION

The present invention relates to an apparatus for discriminating a particle aggregation pattern and, more particularly, to a particle aggregation pattern discriminating apparatus which is suitable to discriminate an aggregation pattern of blood particles by a microtiter method which is used in discriminating blood types and in antigen and antibody detection.

BACKGROUND OF THE INVENTION

In the medical field, hitherto, there has widely been used a method whereby aggregation patterns of blood particles, latex particles, carbon particles, and the like are discriminated and various components (for instance, blood type and various antibodies, or various proteins, etc.) in the blood, viruses, and the like are detected and analyzed. As a method of discriminating the aggregation patterns, a microtiter method is frequently used.

According to the microtiter method in immunology measurement, the blood is aggregated on a microplate by a predetermined method, and the presence or absence of the aggregation is examined or an area or the like of the aggregation pattern is calculated, thereby executing a fine measurement of an immune component. Hitherto, the presence or absence of the aggregation has been discriminated by visual observation. However, in recent years, automatization of such a discrimination has also progressed.

In the discrimination of the aggregation pattern, the presence or absence of an aggregation is synthetically judged in a manner such that a distribution of the particles in a well (i.e. reactive vessel) is detected as an area of the portions whose luminance are equal to or less than a predetermined luminance or compared with a reference pattern or a reference non-. aggregation pattern and, further, a continuous stage dilution series of a specimen sample is formed, or the like.

The automatization of the discrimination for the aggregation patterns is accomplished by optical means and electric calculation processing means for electrically processing the aggregation patterns which are obtained by the optical means.

FIG. 9 shows a conventional example. In the conventional example shown in FIG. 9, an aggregation pattern P in a well (reactive vessel) 100A formed on a microplate 100 is optically projected onto a CCD line sensor 101. One of the line sensor 101 or microplate 100 is sequentially finely moved relative to the other in the direction perpendicular to the paper surface, thereby obtaining a (light and dark) two-dimensional image of the aggregation image P. In FIG. 9, reference numeral 102 denotes a light source, 103 indicates an image forming lens, and 104 a lens holder.

However, in the conventional example, the sensor output becomes remarkably dark at both end portions E and F of a window width L as shown in FIG. 10 due to aberrations or the like of the lens holder 104 and lens 103, and if such dark portions are extended, there occurs an inconvenience such that the extraction of the aggregation pattern in the central portion is obstructed. On the other hand, if the obtained data is collected and a solid diagram shown in FIG. 11 is formed and, after that, the aggregation pattern in the central portion is extracted by a proper threshold value, there often occurs an inconvenience such that dark portions are largely displayed as area data as shown, for instance, in FIG. 12 (solid line portions in the diagram) due to influences by light disturbance and electric noise.

It is an object of the invention to reduce the inconveniences of the foregoing conventional example and, more particularly, to provide a particle aggregation pattern discriminating apparatus in which disturbance factors can be effectively eliminated and aggregation pattern data can be effectively extracted, thereby improving the reliability of the whole apparatus.

The present invention preferably comprises a data memory circuit to sequentially store line data of an aggregation pattern which is output from a CCD line sensor at predetermined timings; threshold value specifying means for specifying a predetermined threshold value on the basis of the line data which is stored into the data memory circuit; and pattern area calculating means for extracting the aggregation pattern from the line data in the data memory circuit on the basis of the threshold value specified by the threshold value specifying means and obtaining a shape and an area of the aggregation pattern. The threshold value specifying means has a first maximum value specifying function to obtain the maximum value of each set of line data in the data memory circuit; a second maximum value specifying function to further obtain the maximum value of all of the aforementioned maximum values obtained by the first maximum value specifying function; and a threshold value specifying function to specify a threshold value of a predetermined magnitude on the basis of the maximum value obtained by the operation of the second maximum value specifying function. Due to this, it is intended to accomplish the above object.

BRIEF DESCRIPTION OF THE DRAWINGS

An embodiment of the invention will be described hereinbelow on the basis of the drawings, in which:

FIGS. 9 to 12 are explanatory diagrams showing structure and operation of conventional systems.

DETAILED DESCRIPTION

Figure 1:
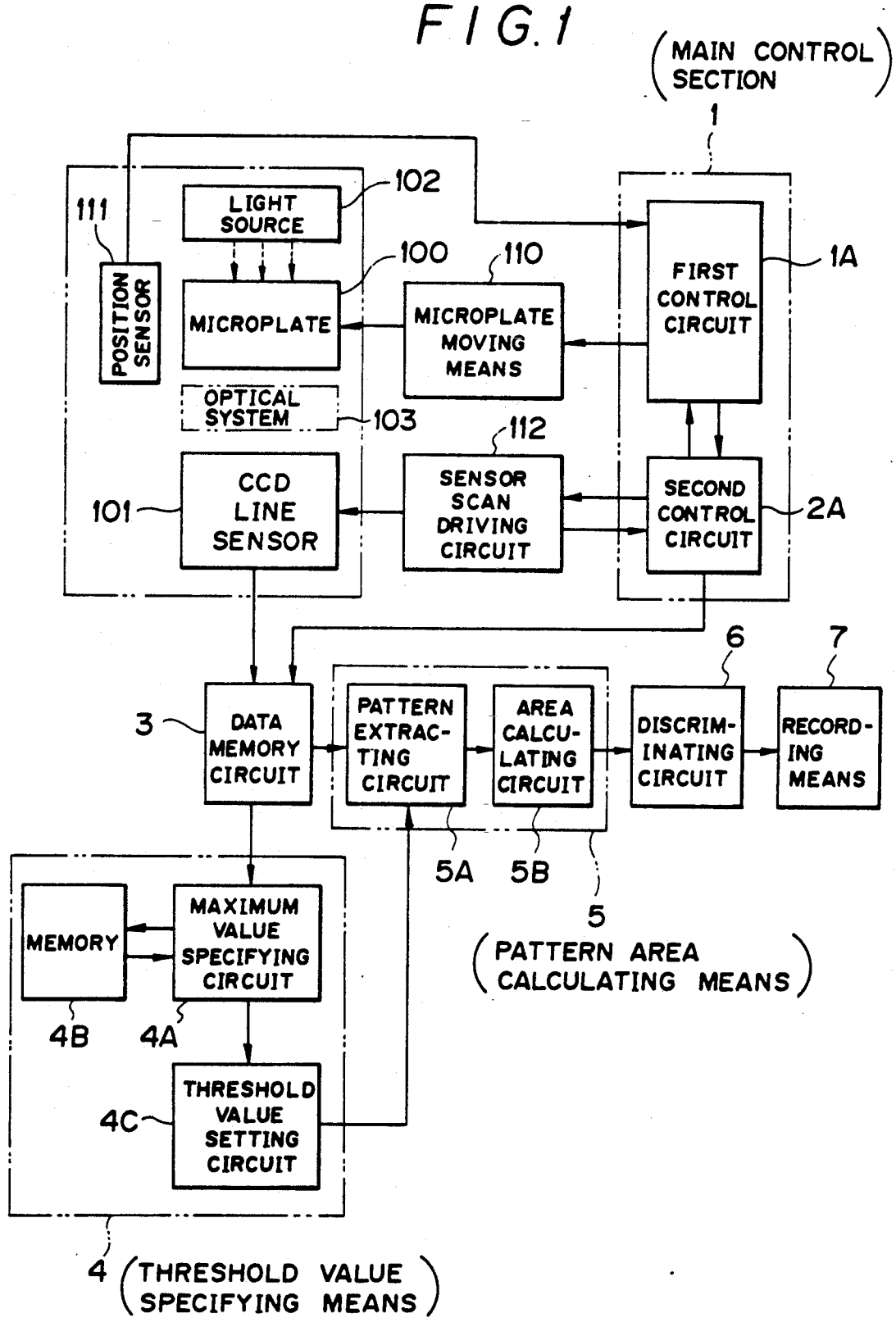
FIG. 1 is a block diagram showing a first embodiment of the invention.
Figure 9:
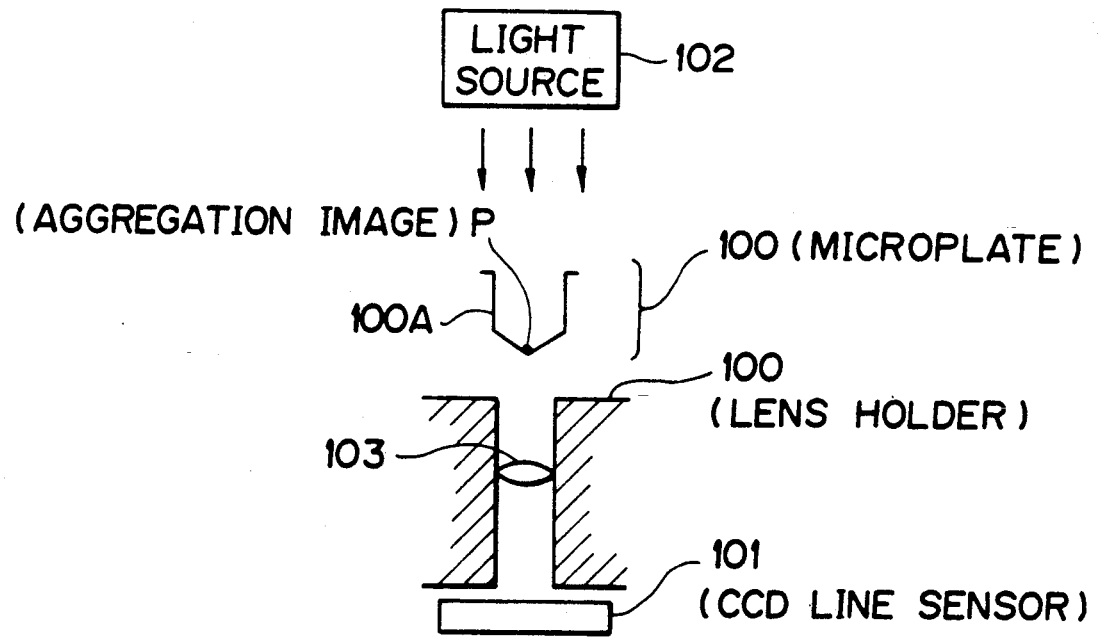

In FIG. 1, the CCD line sensor 101 is arranged below the microplate 100 having a reactive vessel, and an optical system 103 is disposed therebetween in a manner similar to the conventional example shown in FIG. 9 mentioned above. The microplate 100 is driven by microplate moving means 110 and is sequentially moved relative to CCD sensor 101 by a micro distance at a time in a first direction perpendicular to the scanning direction of the CCD line sensor 101 and in a second direction opposite to the first direction. Reference numeral 111 denotes a position detecting sensor. The position detecting sensor 111 decides a reciprocation moving distance of the microplate 100. An output of the sensor 111 is sent to a first control circuit 1A in a main control section 1. Thus, the position of the microplate 100 is always specified and the microplate 100 is moved forward, backward, or stopped as necessary.

Figure 2:
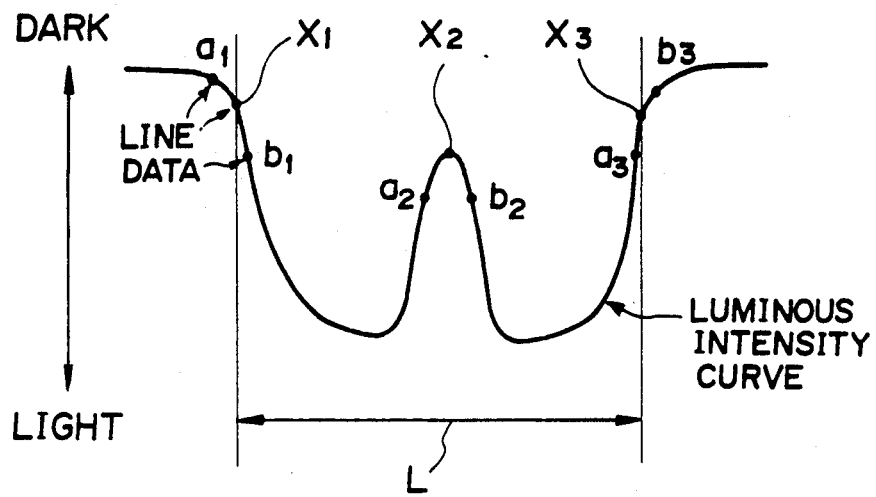
FIG. 2 is an explanatory diagram showing some of the functions of the threshold value specifying means in FIG. 1.
Figure 6:
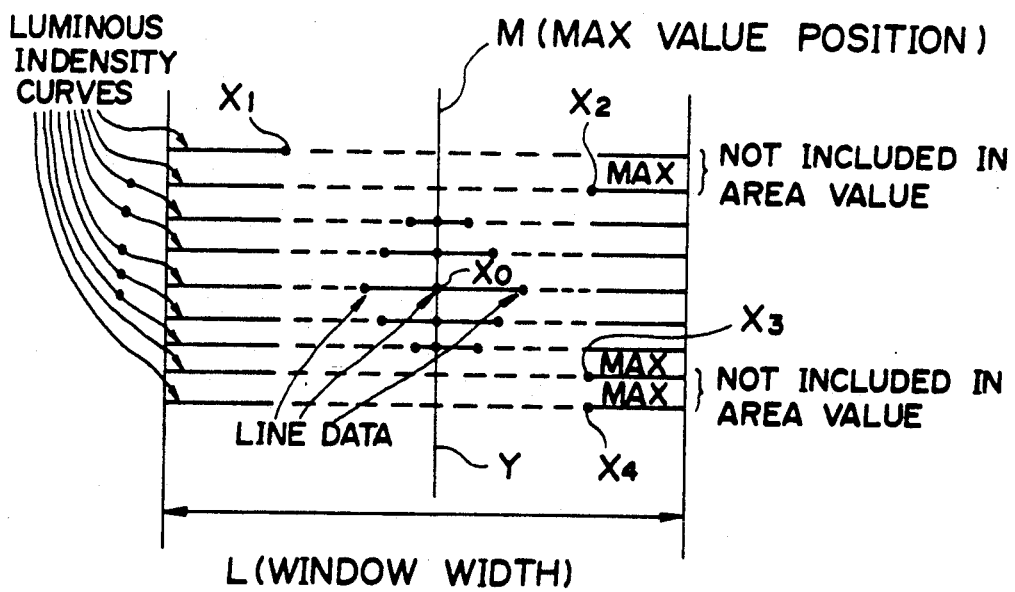
FIG. 6 is an explanatory diagram showing another example of the functions of the threshold value specifying means in FIG. 1.

The CCD line sensor 101 is driven by a sensor scan driving circuit 112, as controlled by second control circuit 2A. The CCD line sensor 101 is made operative and can sequentially convert the particle aggregation patterns on the microplate 100 mentioned above into line data in a state in which the pattern was cut by the sensor 101 at closely spaced intervals. Referring to FIGS. 2, 6 and 11, each set of line data from the CCD line sensor 101 defines a luminous intensity curve which represents a generally one-dimensional component of the two-dimensional aggregation pattern image.

Further, the embodiment shown in FIG. 1 has a data memory circuit 3 to sequentially store the line data which is output from the CCD line sensor 101 at predetermined timings. On the other hand, the apparatus has threshold value specifying means 4 for specifying a predetermined threshold value on the basis of the data stored in the data memory circuit 3; and pattern area calculating means 5 for extracting the particle aggregation pattern from the line data stored in the data memory circuit 3 on the basis of the threshold value specified by the threshold value specifying means 4 and obtaining a shape and an area of the particle aggregation pattern. Reference numeral 6 denotes a discriminating circuit and 7 indicates recording means.

The threshold value specifying means 4 comprises a maximum value specifying circuit 4A to obtain the maximum value of each set of line data; a maximum value memory circuit 4B to store the maximum value which is specified by the maximum value specifying circuit 4A; and a threshold value setting circuit 4C to decide a predetermined threshold value (for instance, a value of ½ of the maximum value) on the basis of the maximum value which is finally determined by the maximum value specifying circuit 4A.

The maximum value specifying circuit 4A has a first maximum value specifying function to obtain a maximum value from each set of line data in the data memory circuit 3, and a second maximum value specifying function to obtain a further, overall maximum value among the maximum values obtained by the first maximum value specifying function. Thus, the overall maximum value is the largest of the previously determined maximum values.

The maximum value of each set of line data is specified as shown, for example, in FIG. 2. That is, a luminous intensity curve of line data as sent from the CCD line sensor 101 is cut by the window width L. There are three data $X_1$, $X_2$, and $X_3$ which are likely to be the desired maximum value in the range of L in FIG. 2. In this case, the first maximum value specifying function immediately operates, selecting two data points "a" and "b" located respectively before and after each value $X_1$, $X_2$ and $X_3$ of the relevant line data. The value $X_n$ which simultaneously satisfies $$X_n > a_n \text{ and } X_n > b_n$$

is specified as a maximum value of the line data.

In the case of FIG. 2, "$X_1 < a_1$, $X_1 > b_1$", "$X_2 > a_2$, $X_2 > b_2$", and "$X_3 > a_3$, $X_3 < b_3$" are obtained. Therefore, in the case of FIG. 2, $X_2$ is specified as a maximum value in the line data, that is, $X_{MAX} = X_2$.

Consequently, according to the first embodiment, only the line data located in the central portion is specified as data regarding the particle aggregation pattern. That is, in the process of the maximum value specifying operation, the disturbance factors for the line data are effectively eliminated, as will become evident below.

Figure 3:
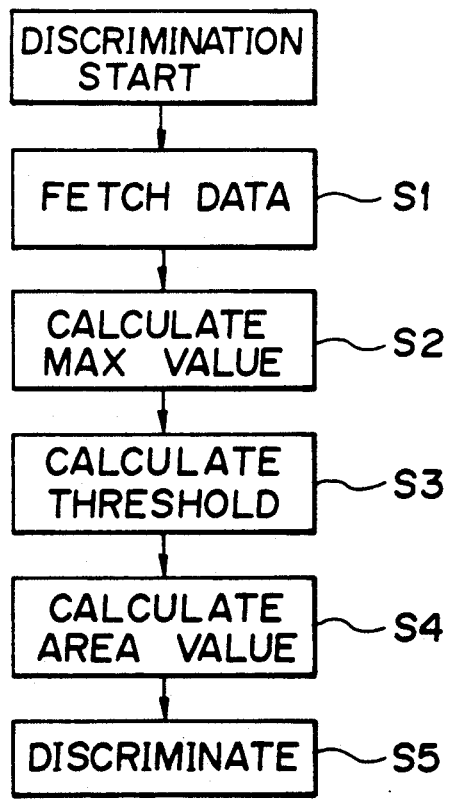
FIG. 3 is a flowchart showing the operation of FIG. 1.

FIG. 3 is a flowchart showing the operation of the whole apparatus. The discriminating operation of a particle aggregation pattern is executed by five steps from the data fetching in the first step S1 to the discrimination in the fifth step S5.

Further, the pattern area calculating means 5 has an area calculation data specifying function to set a line segment in a range starting from the maximum value in each of the line data mentioned above and reaching the threshold value to data for calculation of a pattern area, and a pattern area calculating function to calculate an area of the aggregation pattern on the basis of the data for calculation of the pattern areas of all of the line data which are specified by the area calculation data specifying function. Explaining further in detail, the pattern area calculating means 5 comprises an aggregation pattern extracting circuit 5A to extract line elements for a particle aggregation pattern from the line data in the data memory circuit 3 on the basis of the threshold value of a predetermined level which is output from the threshold value specifying circuit 4C mentioned above, and an area calculating circuit 5B for adding the line elements extracted by the aggregation pattern extracting circuit 5A and calculating an area of the aggregation pattern.

Figure 4:
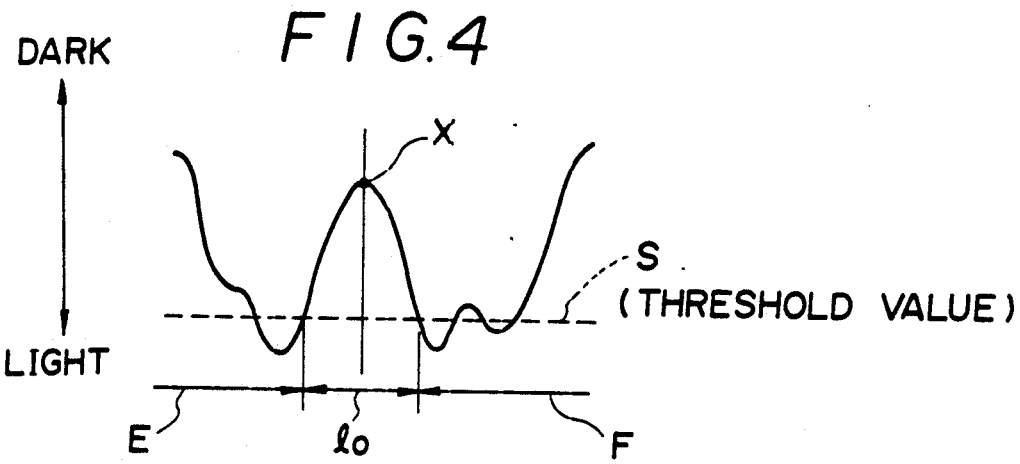
FIG. 4 is an explanatory diagram showing some of the functions of the pattern area calculating means in FIG. 1.

The pattern extracting circuit 5A fetches only the line segment data located between the maximum value X and the threshold value S as area calculating data as shown in FIG. 4. Therefore, as shown in FIG. 4, the areas indicated at E and F, which represent disturbance factors, are actively eliminated from the area calculation data.

Referring to FIG. 4, only that portion of the line data between maximum value X and threshold value S is considered by circuit 5A, such that circuit 5A defines a line segment having length $l_o$. After all of the line segments (see FIG. 6) have been determined by circuit 5A, then circuit 5B adds the lengths of the line segments. The resulting sum is used to approximate the hatched area A in FIG. 11.

As mentioned above, according to the embodiment, there is an advantage such that the influences by the disturbance light and noise are eliminated and the area data due to only the particle aggregation pattern can be calculated.

Figure 5:
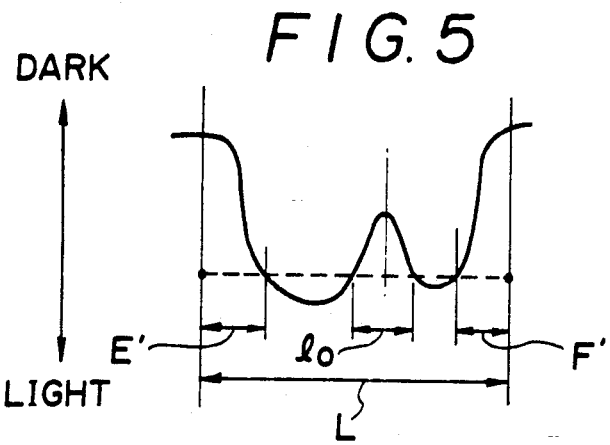
FIG. 5 is an explanatory diagram showing another example of the functions of the pattern area calculating means in FIG. 1.

The above embodiment has been described with respect to the case where only the line segment data locating between the maximum value X and the threshold value S is fetched as data for area calculation by the pattern extracting circuit 5A. However, it is also possible to use other equivalent methods such that, as shown in FIG. 5, with respect to the line segment data of data portions E' and F' which are continuous at both ends of the window width L, they are not used to calculate an area value if a similar equivalent method is used.

On the other hand, in the embodiment, in the case where disturbance elements occur irregularly and the maximum value $X_n$ of each set of line data is distributed as shown in FIG. 6, it is also possible to use a maximum value specifying function such that among the maximum values specified by the foregoing first maximum value specifying function, the maximum values of all of the line data are selected and specified from a plurality of maximum values which are located in almost the central portion of the window L and which exist on almost the same line (line Y in FIG. 6).

Thus, if the overall maximum value is chosen from only the maximum values close to line Y, there is an advantage such that the effect of maximum values (disturbance elements) which deviate from the maximum value line Y (see $X_1$-$X_4$ in FIG. 6) in the central portion of window L can be completely eliminated.

It should be understood from the above description that the main control section 1, the threshold value specifying means 4, and the pattern area calculating means 5 may be implemented with a conventional microprocessor circuit.

A second embodiment will now be described on the basis of FIG. 7. The same component elements as those in the embodiment of FIG. 1 are designated by the same reference numerals.

Figure 7:
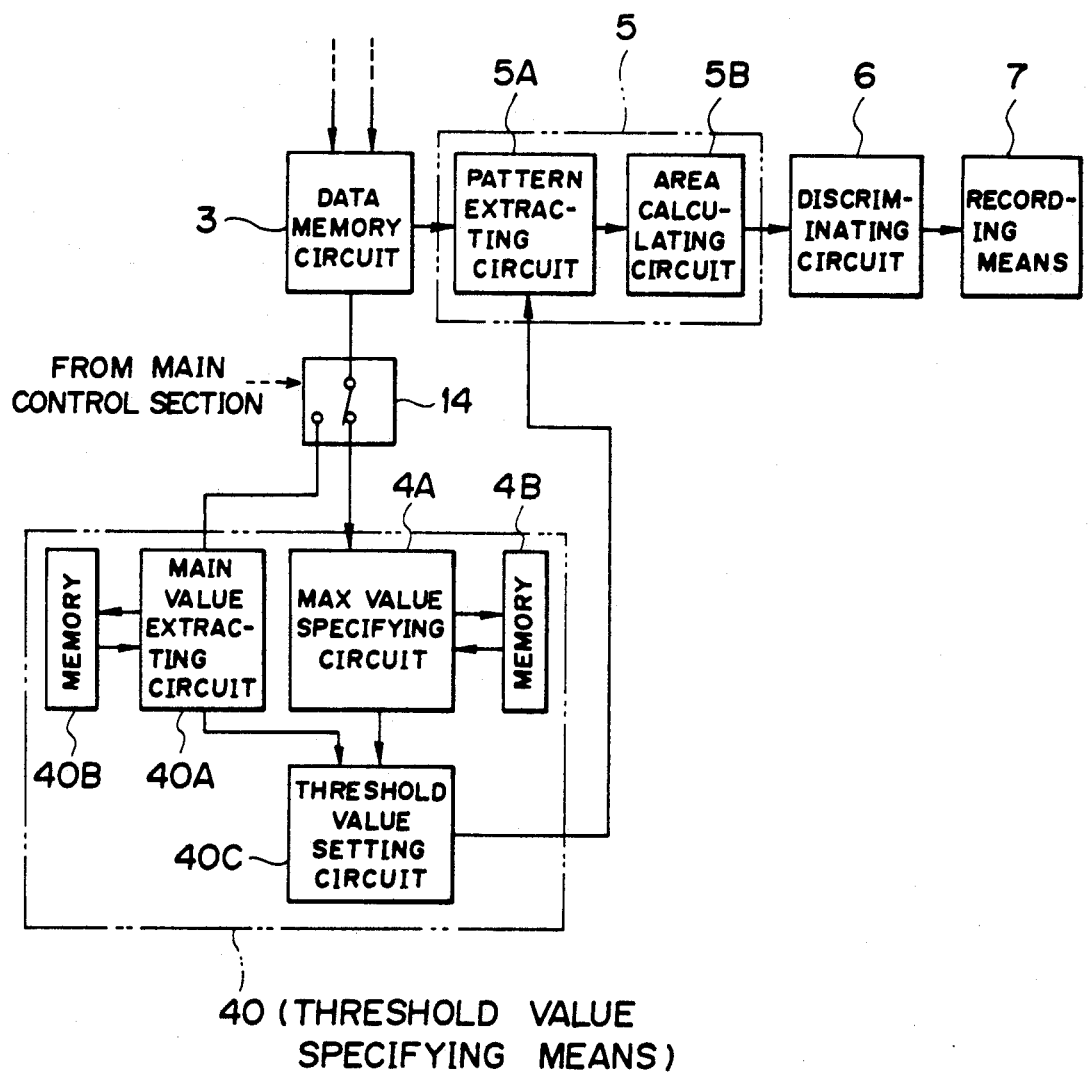
FIG. 7 is an explanatory block diagram showing a second embodiment of the invention.

In the embodiment shown in FIG. 7, a minimum value extracting circuit 40A is also provided in the threshold value specifying circuit 40, and a threshold value can also be determined on the basis of an output of the minimum value extracting circuit 40A. That is, an output stage of the data memory circuit 3 is input to threshold value specifying means 40 through a change-over switch 14. The minimum value extracting circuit 40A and the maximum value specifying circuit 4A are provided in the threshold value specifying means 40. Outputs of the minimum value extracting circuit 40A and the maximum value specifying circuit 4A are input to a threshold value setting circuit 40C provided on the output sides of them. Reference numerals 4B and 40B denote memories provided for the maximum value specifying circuit 4A and the minimum value extracting circuit 40A, respectively.

The minimum value extracting circuit 40A has a first minimum value specifying function to obtain a minimum value from each set of line data in the data memory circuit 3 with the aid of the memory 40B, and a second minimum value specifying function to further obtain one minimum value from the set of minimum values obtained by the first minimum value specifying function. The threshold value setting circuit 40C has a function equivalent to the threshold value setting circuit 4C in the embodiment of FIG. 1 mentioned above, and also has a threshold value specifying function by another method such that a threshold value of a predetermined magnitude is determined on the basis of the minimum value obtained by the operation of the foregoing second minimum value specifying function.

Figure 8:
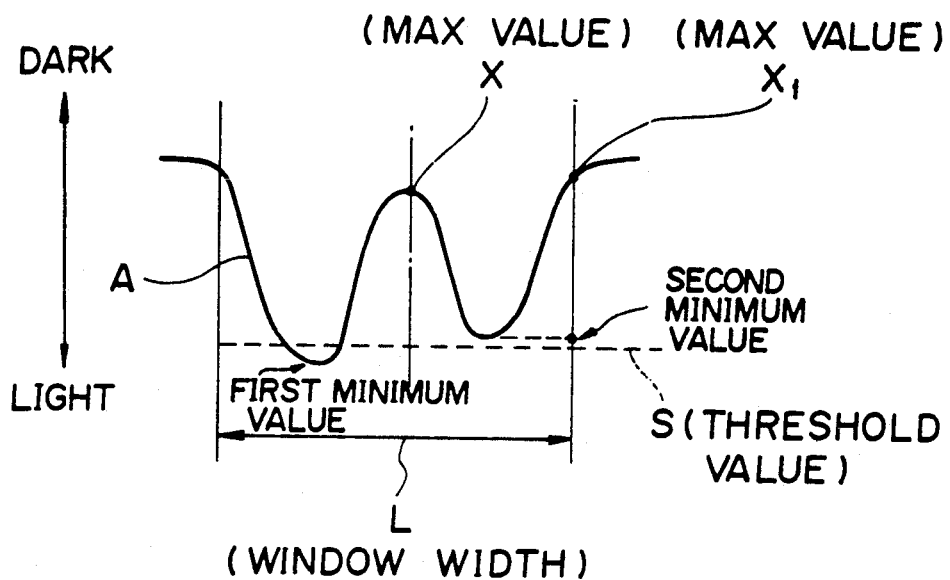
FIG. 8 is an explanatory diagram showing the operation of FIG. 7.

A threshold value determining method based on the minimum value of the line data will now be further described in detail. First, the first minimum value specifying function of the minimum value extracting circuit 40A operates for each set of line data. Referring to FIG. 8, the minimum data points located on the left and right sides of the maximum value of each set of line data are respectively specified as first and second minimum values. Then, the second minimum value specifying function operates and the maximum values between the first and second minimum values of all of the line data specified by the foregoing first minimum value specifying function are specified as a minimum value regarding the relevant aggregation pattern data.

The threshold S in FIG. 8 is not high enough to permit circuit 5A to define the required line segments as illustrated in FIG. 4. If the second minimum value in FIG. 8 is chosen by the second minimum value specifying function, then the threshold value S can be required to be at least as large as the second minimum value. This ensures that threshold value S will be large enough to permit circuit 5A to define the line segments as illustrated in FIG. 4.

Therefore, upon setting of the threshold value using the minimum value extracting circuit 40A in the second embodiment, for instance, an inconvenience such that the maximum value cannot be specified even if, for instance, the threshold value S as set as shown in FIG. 8 can be completely eliminated. The measuring accuracy and reliability of the whole apparatus can be remarkably improved.

The other constructions and operations are the same as those in the embodiment of FIG. 1 mentioned above.

As mentioned above, according to the invention, it is possible to provide an excellent particle aggregation pattern discriminating apparatus which is not obtained hitherto and in which the maximum value (or the minimum value if necessary) of the particle aggregation pattern data can be obtained at a high precision without being influenced by disturbances. The threshold value can be arbitrarily accurately set without being influenced by the disturbances on the basis of the maximum value, and a shape and an area which are necessary to discriminate a particle aggregation pattern can be detected and specified at a high accuracy, so that adverse influences by the disturbances can be eliminated and the reliability of the whole apparatus can be remarkably improved.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an apparatus for discriminating a particle aggregation pattern, including a data memory circuit to sequentially store line data of an aggregation pattern which is output from a CCD line sensor at predetermined timings; threshold value specifying means for specifying a threshold value on the basis of the line data which is stored into the data memory circuit; and pattern area calculating means for extracting an aggregation pattern from the line data in the data memory circuit on the basis of the threshold value and obtaining a shape and an area of said aggregation pattern, the improvement comprising:

said threshold value specifying means having a first maximum value specifying means for obtaining a maximum value of each set of line data in the data memory circuit, a second maximum value specifying means for obtaining a further maximum value among the maximum values which were obtained by said first maximum value specifying means, and means for specifying a threshold value on the basis of the further maximum value obtained by the operation of the second maximum value specifying means.

2. An apparatus for discriminating a particle aggregation pattern according to claim 1, wherein the first maximum value specifying means functions in a manner such that when a possible maximum value X in the line data is specified, two line data points a and b respectively located sequentially before and after the possible maximum value X are selected, and in the case where the values of points a and b simultaneously satisfy $X > a$ and $X > b$, X is specified as the maximum value of the associated set of line data.

3. An apparatus for discriminating a particle aggregation pattern according to claim 2, wherein the pattern area calculating means has an area calculation data specifying function for setting line segments which each represent a distance, in a scanning direction of the CCD sensor, between two threshold value points in a respective set of line data, said threshold value points being the closest threshold value points to the associated maximum value and being on opposite sides thereof, and said pattern area calculating means having a pattern area calculating function for calculating an area of the aggregation pattern on the basis of the line segments specified by the area calculation data specifying function.

4. An apparatus for discriminating a particle aggregation pattern according to claim 1, wherein the second maximum value specifying means functions in a manner such that among the maximum values specified by the first maximum value specifying means, if a plurality of the maximum values are located in a central portion of a scanning window associated with said CCD sensor and exist on almost the same line, then the further maximum value is specified only from said plurality of maximum values.

5. An apparatus for discriminating a particle aggregation pattern according to claim 4, wherein the pattern area calculating means has an area calculation data specifying function for setting line segments which each represent a distance, in a scanning direction of the CCD sensor, between two threshold value points in a respective set of line data, said threshold value points being the closest threshold value points to the associated maximum value and being on opposite sides thereof, and said pattern area calculating means having a pattern area calculating function for calculating an area of the aggregation pattern on the basis of the line segments specified by the area calculation data specifying function.

6. An apparatus for discriminating a particle aggregation pattern according to claim 1, wherein the pattern area calculating means has an area calculation data specifying function for setting line segments which each represent a distance, in a scanning direction of the CCD sensor, between two threshold value points in a respective set of line data, said threshold value points being the closest threshold value points to the associated maximum value and being on opposite sides thereof, and said pattern area calculating means having a pattern area calculating function for calculating an area of the aggregation pattern on the basis of the line segments specified by the area calculation data specifying function.

7. In an apparatus for discriminating a particle aggregation pattern, including a data memory circuit to sequentially store line data of an aggregation pattern which is output from a CCD line sensor at predetermined timings; threshold value specifying means for specifying a threshold value on the basis of the line data which is stored into the data memory circuit; and pattern area calculating means for extracting an aggregation pattern from the line data in the data memory circuit on the basis of the threshold value specified by the threshold value specifying means and obtaining a shape and an area of said aggregation pattern, the improvement comprising:

said threshold value specifying means having a first minimum value specifying means for obtaining a minimum value of each set of line data in the data memory circuit, means for selecting one of the minimum values which were obtained by said first minimum value specifying means, and means for specifying a threshold value on the basis of the one minimum value.

8. An apparatus for discriminating a particle aggregation pattern according to claim 7, wherein the first minimum value specifying means determines first and second minimum data values which are respectively located on the left and right sides of the maximum value of each set of line data, and said means for selecting one value specifies said one value by obtaining a maximum value among the first and second minimum values of all of the line data specified by the first minimum value specifying means.

9. An apparatus for discriminating a particle aggregation pattern according to claim 8, wherein the pattern area calculating means has an area calculation data specifying function for setting line segments which each represent a distance, in a scanning direction of the CCD sensor, between two threshold value points in a respective set of line data, said threshold value points being the closest threshold value points to the associated maximum value and being on opposite sides thereof, and said pattern area calculating means having a pattern area calculating function for calculating an area of the aggregation pattern on the basis of the line segments specified by the area calculation data specifying function.

10. An apparatus for discriminating a particle aggregation pattern according to claim 7, wherein the pattern area calculating means has an area calculation data specifying function for setting line segments which each represent a distance, in a scanning direction of the CCD sensor, between two threshold value points in a respective set of line data, said threshold value points being the closest threshold value points to the associated maximum value and being on opposite sides thereof, and said pattern area calculating means having a pattern area calculating function for calculating an area of the aggregation pattern on the basis of the line segments specified by the area calculation data specifying function.

* * * * *